US012766242B2

(12) United States Patent
Carpenter

(10) Patent No.: US 12,766,242 B2
(45) Date of Patent: Oct. 20, 2026

(54) STORAGE CONTAINER FOR A MEDICAMENT DELIVERY DEVICE

(71) Applicant: SHL Medical AG, Zug (CH)

(72) Inventor: Lucas Carpenter, Taoyuan City (TW)

(73) Assignee: SHL Medical AG, Zug (CH)

(*) Notice: Subject to any disclaimer, the term of this patent is extended or adjusted under 35 U.S.C. 154(b) by 333 days.

(21) Appl. No.: 18/683,584

(22) PCT Filed: Aug. 18, 2022

(86) PCT No.: PCT/EP2022/073115

§ 371 (c)(1),
(2) Date: Feb. 14, 2024

(87) PCT Pub. No.: WO2023/025662

PCT Pub. Date: Mar. 2, 2023

(65) Prior Publication Data

US 2026/0166216 A1 Jun. 18, 2026

(30) Foreign Application Priority Data

Aug. 24, 2021 (EP) .................................... 21192815

(51) Int. Cl.
*A61M 5/00* (2006.01)

(52) U.S. Cl.
CPC .................................. *A61M 5/002* (2013.01)

(58) Field of Classification Search
CPC .................................................... A61M 5/002
USPC ......................... 206/363, 364, 365, 438, 571
See application file for complete search history.

(56) References Cited

U.S. PATENT DOCUMENTS 4,226,358 A 10/1980 Ottow
5,293,993 A 3/1994 Yates
8,479,919 B2 * 7/2013 Kaplan .................... G09F 3/10
40/310
2004/0069667 A1 4/2004 Tomellini
2009/0200185 A1 * 8/2009 Follman ........... A61B 5/150809
206/364
2010/0059560 A1 * 3/2010 Lanum .................. A61B 50/31
224/257

(Continued)

FOREIGN PATENT DOCUMENTS

EP 2021056 B1 11/2018
EP 2298224 B1 4/2020

(Continued)

OTHER PUBLICATIONS

International Search Report and Written Opinion for corresponding PCT application No. PCT/EP2022/073115 dated Dec. 2, 2022.

*Primary Examiner* — Luan K Bui
(74) *Attorney, Agent, or Firm* — McDonnell Boehnen Hulbert & Berghoff LLP

(57) ABSTRACT

The present disclosure provides a storage container for a medicament delivery device, the storage container comprising a first part and a second part, where the first part is attached to the second part. The first part comprises a first wall defining a first cavity, and the second part comprises a second wall defining a second cavity. The storage container is configured to change shape from a first configuration for storing a medicament delivery device prior to use to a second configuration for storing a used medicament delivery device.

12 Claims, 13 Drawing Sheets

(56) References Cited

U.S. PATENT DOCUMENTS

| | | | | |
|---|---|---|---|---|
| 2011/0071572 | A1* | 3/2011 | Sixto | A61B 17/8014 606/286 |
| 2014/0262884 | A1* | 9/2014 | Priebe | A61M 5/321 206/538 |
| 2015/0164743 | A1* | 6/2015 | Janson | A61J 1/05 206/525 |
| 2016/0198990 | A1* | 7/2016 | Betancur | B01L 9/06 206/363 |
| 2018/0235842 | A1 | 8/2018 | Tennican | |
| 2021/0069406 | A1 | 3/2021 | Politis | |
| 2021/0252209 | A1* | 8/2021 | Nicolas | A61B 50/3001 |
| 2023/0248898 | A1* | 8/2023 | Cook | A61M 5/001 604/500 |

FOREIGN PATENT DOCUMENTS

| | | | |
|---|---|---|---|
| GB | 2485920 | B | 8/2012 |
| WO | 2009053693 | A1 | 4/2009 |

* cited by examiner

Figure 23
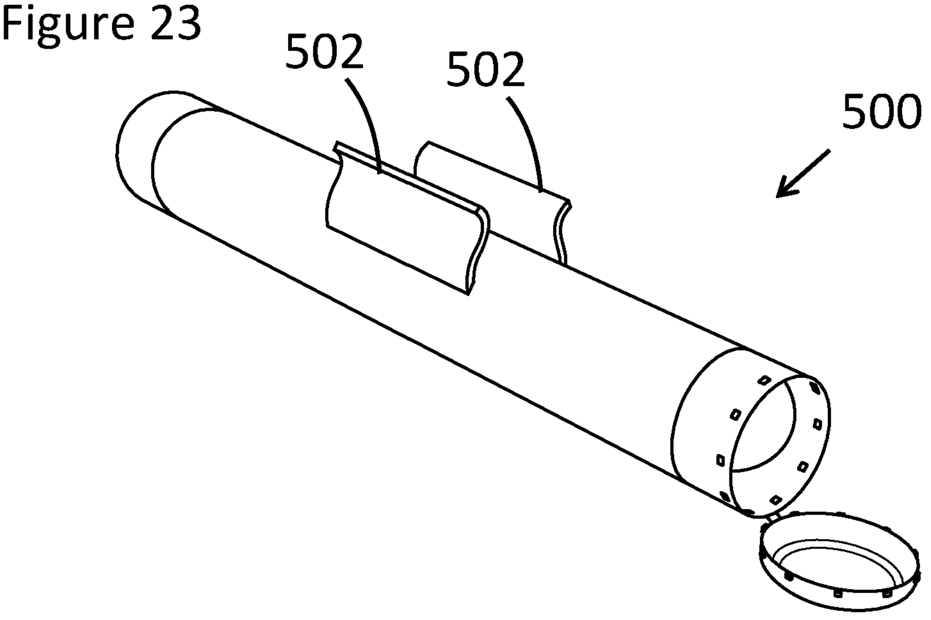
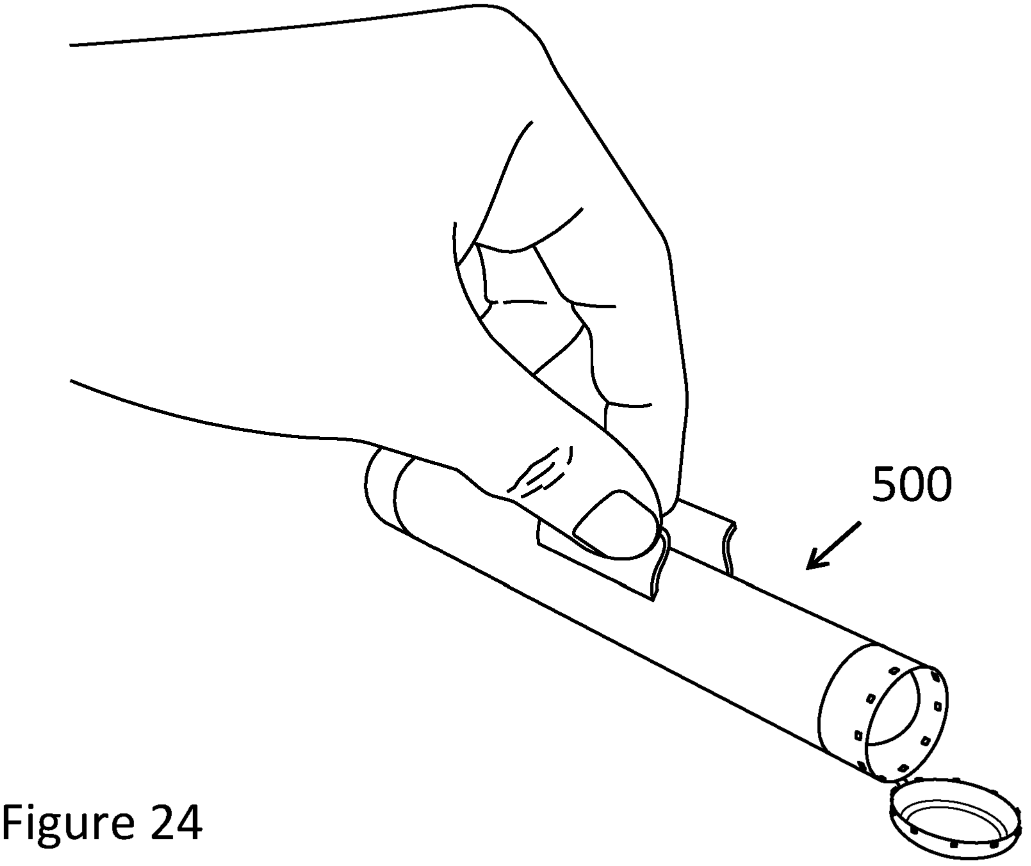
Figure 24

Figure 25
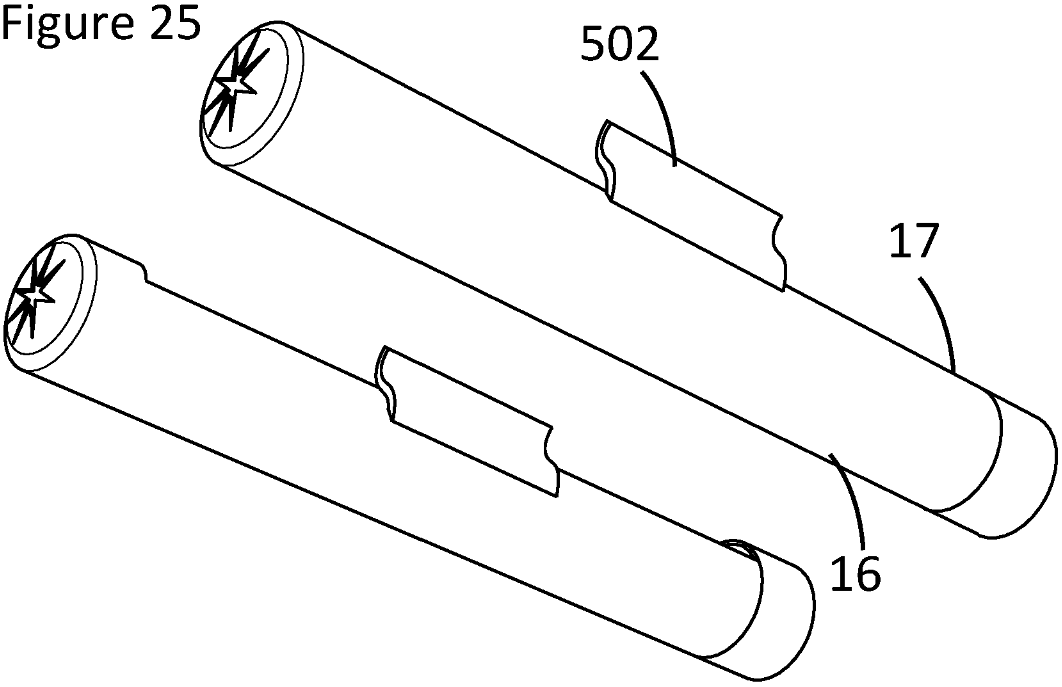
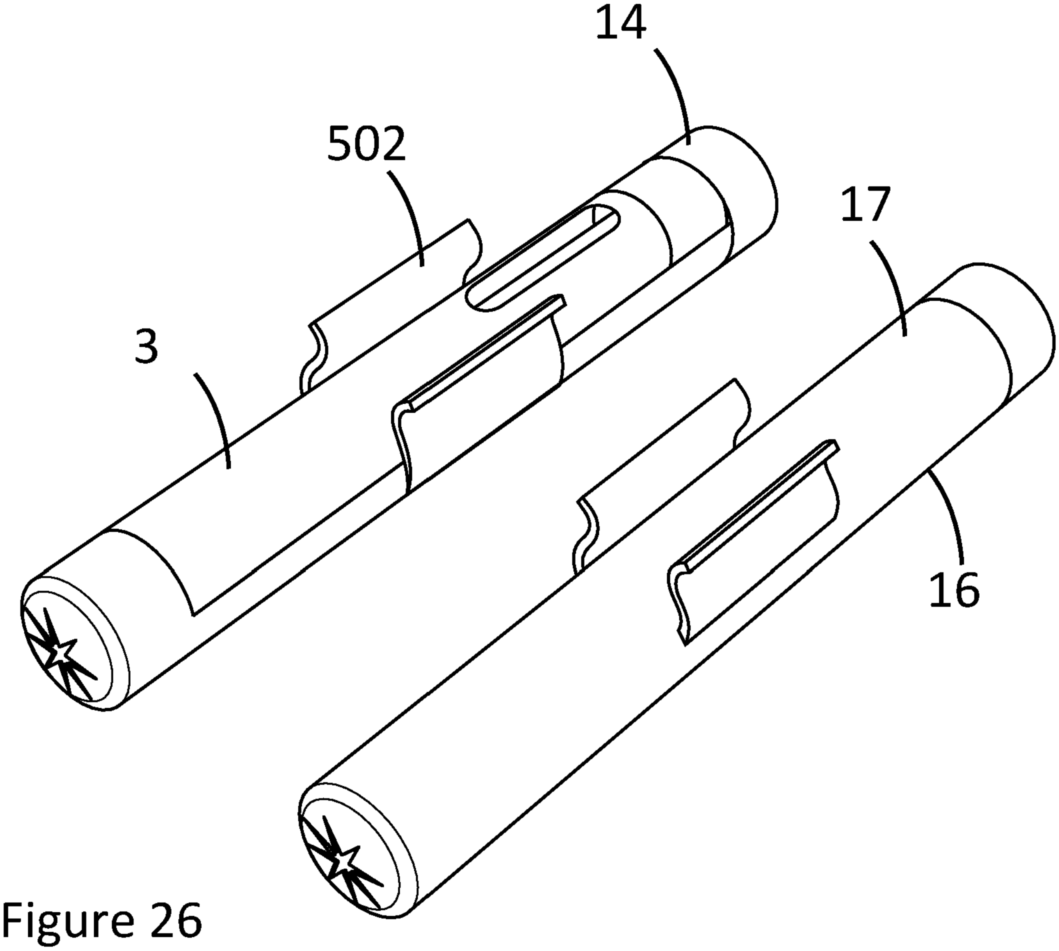
Figure 26

STORAGE CONTAINER FOR A MEDICAMENT DELIVERY DEVICE

CROSS-REFERENCE TO RELATED APPLICATIONS

The present application is a U.S. National Phase Application pursuant to 35 U.S.C. § 371 of International Application No. PCT/EP2022/073115 filed Aug. 18, 2022, which claims priority to (i) European Patent Application No. 21192815.5 filed Aug. 24, 2021. The entire disclosure contents of these applications are herewith incorporated by reference into the present application.

TECHNICAL FIELD

The present disclosure relates to storage containers for medicament delivery devices. In particular, the present disclosure relates to storage containers that are configured to change shape from a first configuration for storing a medicament delivery device prior to use to a second configuration for storing a used medicament delivery device.

BACKGROUND

In hospitals or other medical facilities, containers for receiving articles such as sharps (used syringes, etc.) are known and some of these are arranged so that they can be locked closed prior to incineration. Disposable medicament delivery device containers in general provide a sealed environment which will reduce the possibility of contact by the handler with the secured contents. Nevertheless, the applicant has appreciated that there is still further scope for improvement of the packaging of medical delivery devices having sharps such as those described in WO2009/053693.

Medicament delivery devices or on-body devices, such as hypodermic syringes, with needles, auto-injectors, safety syringes, and pen-injectors are generally known for the self-administration of a medicament by patients without formal medical training. As just one example, patients suffering from diabetes may require repeated injections of insulin. Other patients may require regular injections of other types of medicaments, such as a growth hormone or biological medicaments. Therefore, to facilitate medication delivery for the patients, there is a demand to design medicament delivery devices with multiple automatic functions, predetermined dosage and assembled with a medicament container. Some of the medicament delivery devices are single use devices and disposable after use, other medicament delivery devices may have reusable parts, and only the sharps or contaminated parts such as needles, tubes or nozzles are disposed after use. But in a private or non-medical environment a safe storage of sharps is also advantageous.

EP 2 298 224 A2 describes an example of a shipping container integrating a sharps disposal container with a new product storage container for shipping. The storage container stores a new product. A sharps disposal container receives used sharps. One of the storage container and the sharps disposal container is disposed within the other of the storage container and the sharps disposal container for shipping. A lid is adapted to be connected to the outermost container of the sharps disposal container and the storage container for shipping and to a top of the sharps disposal container for receiving used sharps.

BRIEF DESCRIPTION

The present disclosure is applicable to a number of medical devices, in particular medicament delivery devices including, but not limited to, devices that automatically, semi-automatically or manually deliver one or more doses of medicament through injection (needle and needleless). For example, this could include devices comprising sharps such as hypodermic syringes, auto-injectors, safety syringes, pen-injectors or the like. Further, the disclosure is applicable to a number of packaging containers and packaging materials.

An aspect concerns a storage container for a medicament delivery device, the storage container comprising a first part and a second part, wherein the first part is attached to the second part, wherein the first part comprises a first wall defining a first cavity, wherein the second part comprises a second wall defining a second cavity, wherein the storage container is configured to change shape from a first configuration for storing a medicament delivery device prior to use to a second configuration for storing a used medicament delivery device. This can provide a storage container that can store an unused device and then subsequently store a used device providing a dual use for the storage container.

Optionally the second wall is in the first cavity in the first configuration. This can provide a compact storage of the transformable part before use of the medicament delivery device.

Optionally in the first configuration the second cavity is shaped to snugly receive said medicament delivery device prior to use. This can provide a compact storage of the transformable part before use of the medicament delivery device.

Optionally the second wall is flexible. This can provide an easy transformation of the storage container into a container for disposable medicament delivery devices.

Optionally the second wall is configured to invert from a first position in the first configuration to a second position in the second configuration, wherein the second wall defines a third cavity when in the second position. This can provide an easy transformation of the storage container into a container for disposable medicament delivery devices.

Optionally the third cavity is the same shape as the second cavity. This can provide a compact storage of the transformable part before use of the medicament delivery device.

Optionally a combination of the first cavity and the third cavity is shaped to snugly receive said used medicament delivery device. This can provide a compact storage of the transformable part before use of the medicament delivery device.

Optionally the wall of the first part is configured to snugly receive the wall of the second part. This can provide a compact storage of the transformable part before use of the medicament delivery device.

Optionally the storage container further comprises closing members for enclosing the disposable medicament delivery device in the storage container when in the second configuration.

Optionally the first part is attached to the second part by a hinge.

Optionally the first part comprises a first circumferential rim and the second part comprises a second circumferential rim, and the first circumferential rim is attached to the second circumferential rim.

An aspect concerns a method for changing the shape of a storage container according to any one of the preceding claims from the first configuration to the second configuration, comprising the steps of: taking the medicament delivery device out of the storage container when in the first configuration; and moving the second wall out of the first cavity so that the storage container is ready to receive a used medicament delivery device.

Optionally, moving the second wall comprises the step of rotating the second part about a hinge. Optionally, moving the second wall comprises applying a force on the wall of the second part to invert the cavity of the second part.

The invention is defined by the claims, to which reference should now be made. Preferable embodiments of the invention form the subject of the dependent patent claims.

In the present disclosure, when the term "distal direction" is used, this refers to the direction pointing away from the dose delivery site during use of the medicament delivery device. When the term "distal part/end" is used, this refers to the part/end of the delivery device, or the parts/ends of the members thereof, which under use of the medicament delivery device is/are located furthest away from the dose delivery site. Correspondingly, when the term "proximal direction" is used, this refers to the direction pointing towards the dose delivery site during use of the medicament delivery device. When the term "proximal part/end" is used, this refers to the part/end of the delivery device, or the parts/ends of the members thereof, which under use of the medicament delivery device is/are located closest to the dose delivery site.

Further, the terms "longitudinal", "longitudinally", "axially" and "axial" refer to a direction extending from the proximal end to the distal end and along the device or components thereof, typically in the direction of the longest extension of the device and/or component.

Similarly, the terms "transverse", "transversal" and "transversally" refer to a direction generally perpendicular to the longitudinal direction.

Generally, all terms used in the claims are to be interpreted according to their ordinary meaning in the technical field, unless explicitly defined otherwise herein. All references to a/an/the element, apparatus, member, component, means, etc. are to be interpreted openly as referring to at least one instance of the element, apparatus, member component, means, etc., unless explicitly stated otherwise.

The term automatic in conjunction with medical injection device means that, the injector device is able to perform the injection without the user of the device delivering the force needed to expel the medicament during delivery. The force is delivered automatically by a resilient force like a spring or an electric motor or any other suitable means for providing the delivery force.

BRIEF DESCRIPTION OF THE DRAWINGS

Embodiments of the present disclosure will now be described by way of example only and with reference to the accompanying drawings, in which:

FIGS. 20 to 24 show views of another example storage container, shown in various stages of use.

FIGS. 25 to 26 show views of another example storage container, shown in various stages of use.

DETAILED DESCRIPTION

Several example storage containers will now be described. In general, the storage containers are configured to change shape from a first configuration for storing a medicament delivery device prior to use to a second configuration for storing a used medicament delivery device.

Figure 1:
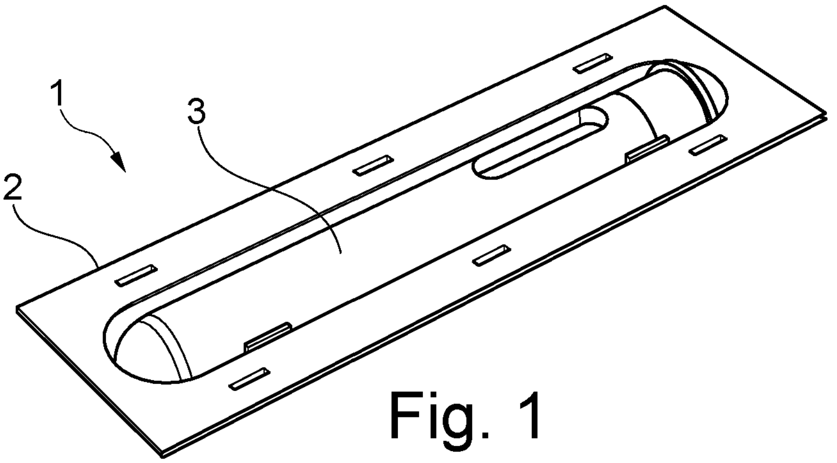
FIG. 1 shows a perspective view of the storage container 1 comprising a medicament delivery device prior to use embedded in one of the parts of the container.
Figure 2:
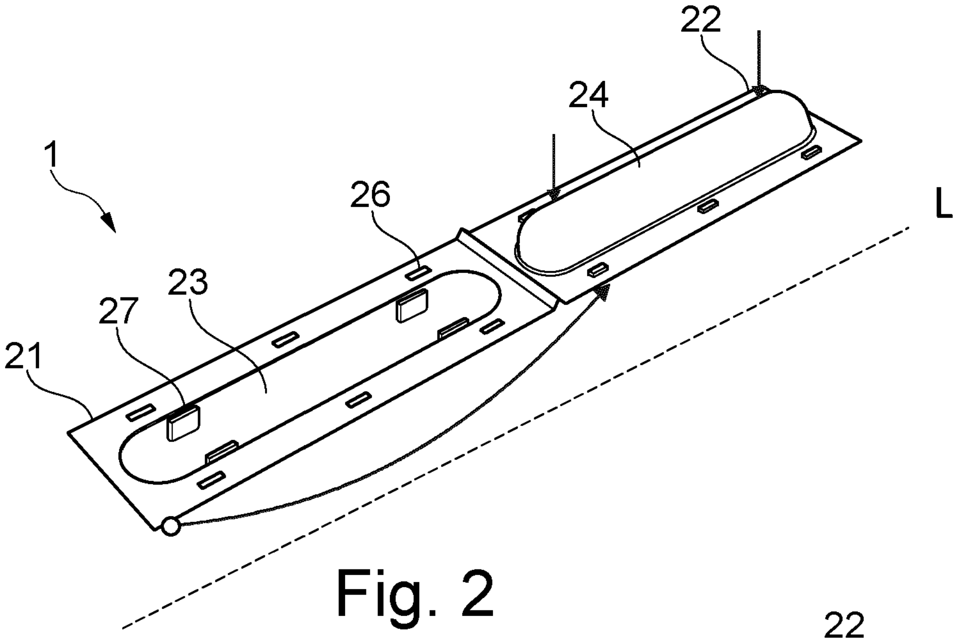
FIG. 2 shows a perspective view of the storage container in an unfolded configuration of the parts.
Figure 3:
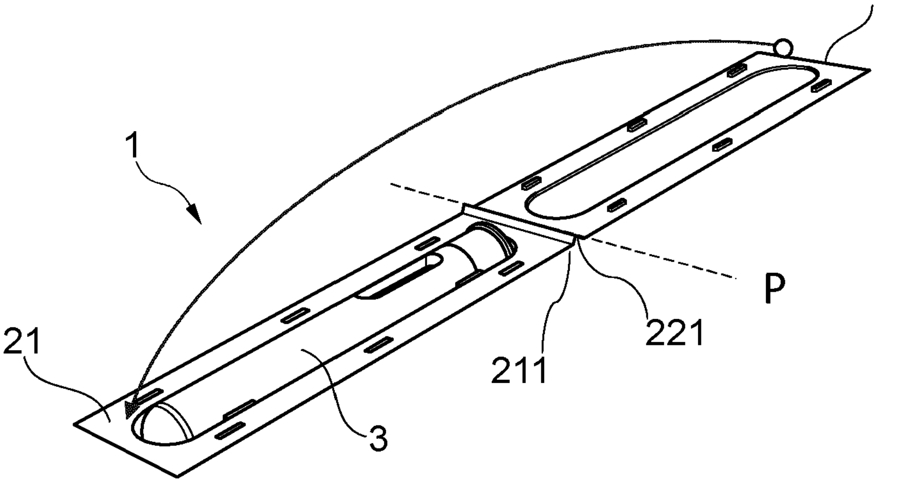
FIG. 3 shows a perspective view of the storage container being converted into a disposable medicament delivery device container.
Figure 4:
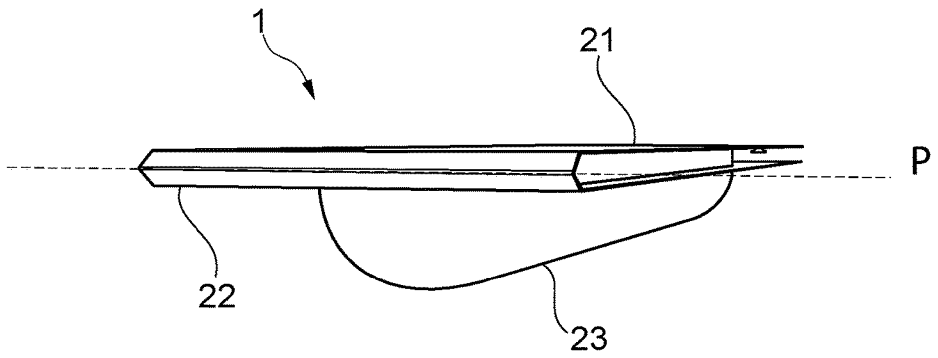
FIG. 4 shows a perspective side view of the storage container 1.
Figure 5:
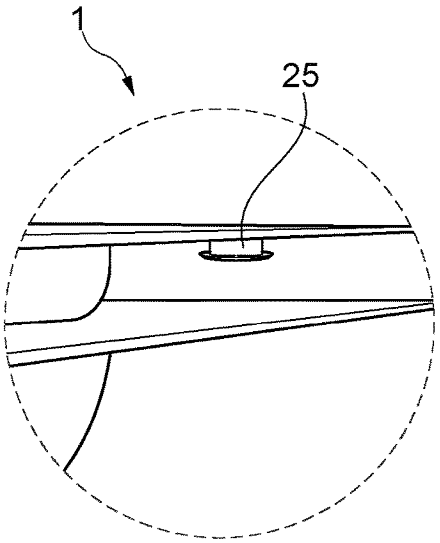
FIG. 5 is a magnification of a section of the container of FIG. 4.

In one embodiment, as shown in FIGS. 1 to 3, the storage container 1 extends in a longitudinal direction along an axis L and comprises two parts 2, which are joined at one of their ends 211, 221 along an axis P perpendicular to the axis L. Instead of a rectangular profile, the container 1 could have any other suitable shape, for example circular or triangular. Each of the parts 21, 22 comprise a first cavity 23 and a second cavity 24, with the storage container being configured for receiving the medicament delivery device 3 for storage and transport. Each part further comprises a flange, which forms a projecting flat rim or collar around the respective cavity and comprises at least one pair of closing members 25, 26 as shown in FIGS. 2 and 5. The at least one pair of closing members comprise one member on each flange of each part configured to cooperate with each other. The storage container 1 further is foldable along the axis P, as shown in FIG. 4, such that one part overlies the other part and the cavity of one of the parts fits into the cavity of the other part when the parts are folded onto each other.

Alternatively, the two parts of the storage container 1 are joined along the longitudinal axis L along a longitudinal side. In this example the storage container 1 is foldable along the longitudinal axis about a hinge extending along the longitudinal side of the join joining the first part to the second part.

The storage container 1 is convertible into a disposable medicament delivery device container by deflection of a portion of one of the parts of the container. The disposable medicament delivery device should be understood as either a single use device or a reusable device which no longer is usable and thus has to be disposed of. FIG. 2 shows the storage container 1 after the medicament delivery device 3 has been taken out of the container 1. The second part 22, which was previously overlaying the first part 21, unfolds out of the first part 21. The first cavity 23 is configured to receive within its cavity the wall of the second part 22 which forms the second cavity 24. When unfolded, the second cavity 24 (which was previously lying within first cavity 23) rotates 180 degrees. This translational movement rotates the opening of the second cavity 24 of the second part 22 by 180 degrees, thus the opening of the second cavity 24 is inverted. Further, holding elements 27 are arranged along the lateral inner sides of the cavities. The holding elements 27 are configured to secure and hold in place the medicament delivery device 3 when the container is configured as a storage container. In this state the holding elements 27 of the first cavity 23 secure and hold the lateral sides of the second cavity 24 of the second part 22 lying within first cavity 23. The holding elements 27 of the second cavity 24 are configured to hold and secure the medicament delivery device being placed within the second cavity 24.

Figure 6:
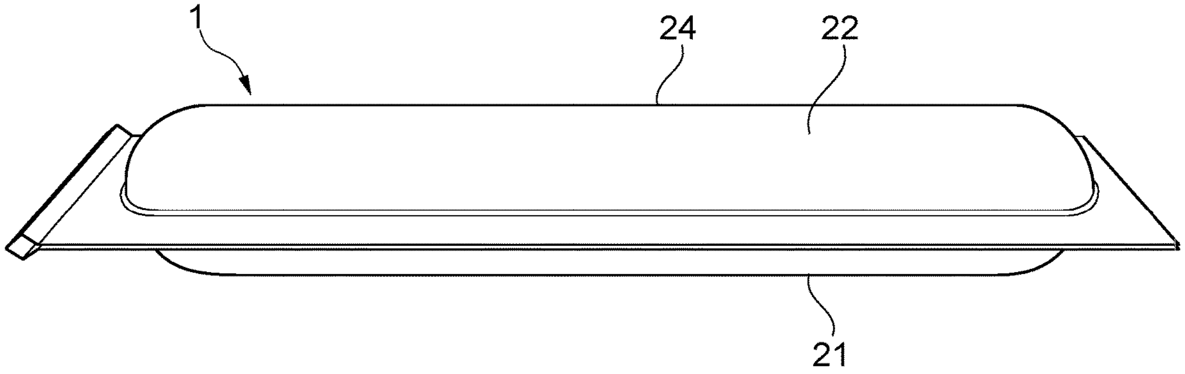
FIG. 6 shows the container 1 as a disposable medicament delivery device container after transformation.
Figure 7:
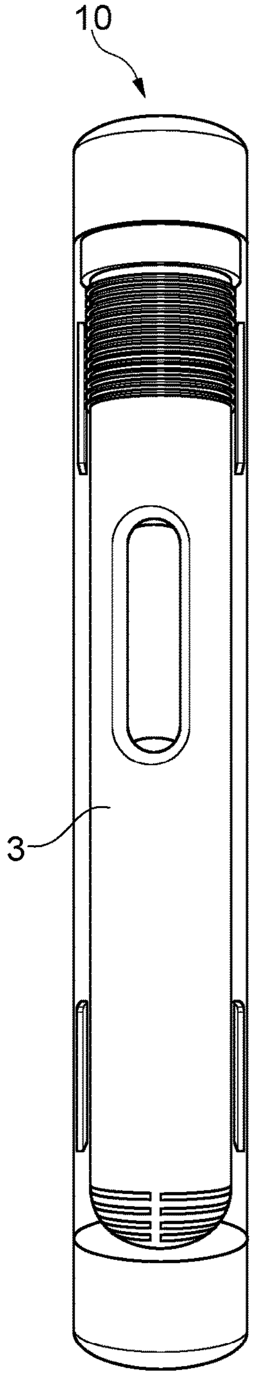
FIG. 7 is a front view of another storage container 10 with a medicament delivery device inside it.

In order to transform the storage container 1 into a disposable medicament delivery device container the user has to apply a force onto the outwardly arched wall of the second part which forms the second cavity 24 of the second part 22 to deflect it until the opening of the second cavity 24 is inverted, i.e. until the outwardly arched wall is an inwardly arched wall creating a third cavity formed by the wall of the second part (and thereby removing the second cavity). As shown in FIG. 3 the medicament delivery device 3, which after use is considered as a disposable medicament delivery device and shall be disposed of, can be laid into the first cavity 23 of the first part 21. The holding elements 27 of the first cavity 23 hold and secure the medicament delivery device 3 when placed into the first cavity 23. Subsequently, the second part 22 can rotate and fold back onto the first part 21 which securely holds the disposable medicament delivery device, i.e. used single use or reusable medicament delivery device, within its first cavity 23 as is shown in FIG. 6. Further the user can squeeze the pair of closing members 25, 26 between their fingers in order to lock both parts 21, 22 together. For example, the at least one pair of closing members is configured such that on one flange of one part a protrusion 25 is arranged, which when this part is folded over the other part, this protrusion 25 fits into a corresponding recess 26, wherein the corresponding recess is arranged on the flange of the other part.

The closing members can be of any suitable type, for example in form of push buttons, snap fit mechanisms, velcro tape, glue, hooks, and/or magnets.

Figure 8:
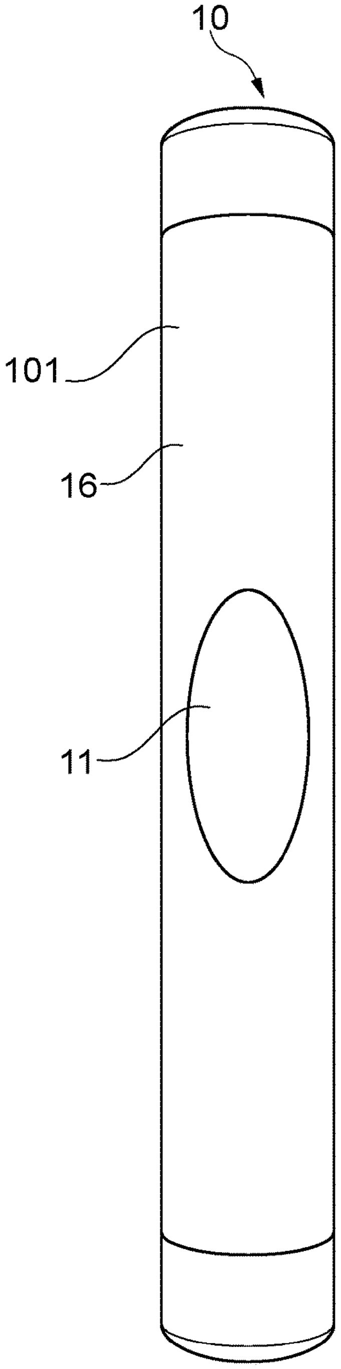
FIG. 8 is a rear view of the container 10 of FIG. 7.
Figure 9:
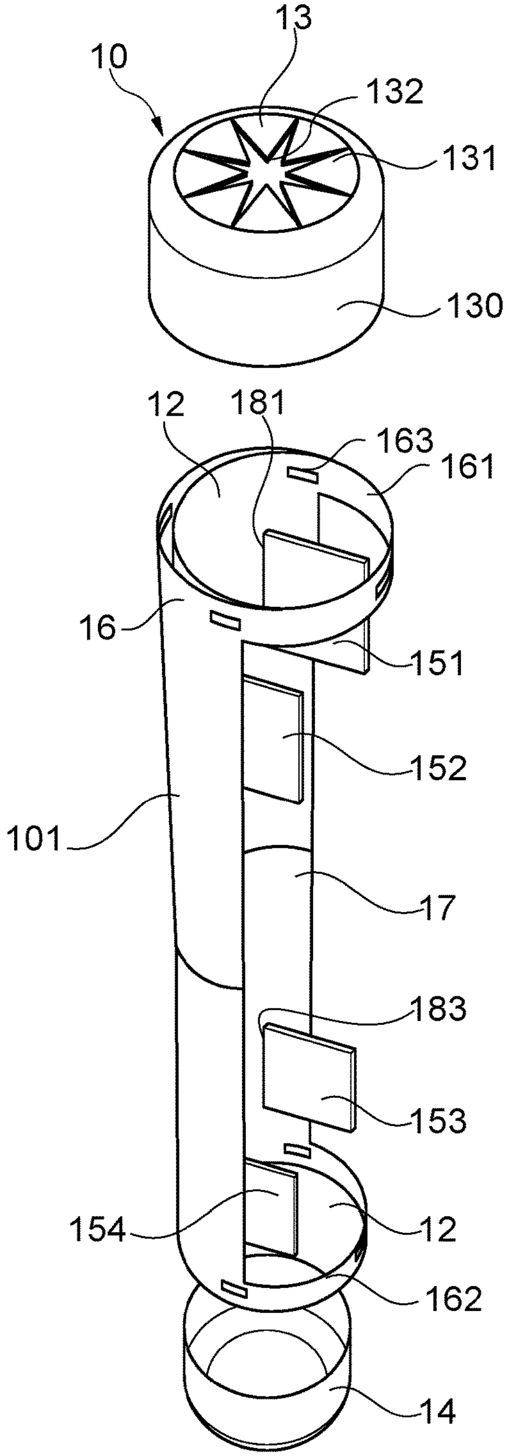
FIG. 9 is an exploded perspective view of the container of FIG. 7 without the medicament delivery device.

FIGS. 7 to 14 illustrate an alternative embodiment, wherein a storage container 10 has a longitudinal tubular shape extending along an axis L and comprises a tubular body 101, the tubular body 101 having a front side and a rear side along the axis L. The tubular body 101 comprises on the front side a central tubular cavity 12 extending from one end to the other end of the tubular body 101. The central tubular cavity 12 has a longitudinal opening; in other words, the central tubular cavity 12 defines a shape of a longitudinally sectioned half tube whereby the ends of the tubular body 101 are open as can be seen in FIG. 9. The central tubular cavity 12 is configured to receive the medicament delivery device 3. On the rear side of the tubular body 101 is a cut out 11. The tubular body comprises two parts 16, 17 in the form of two half-shells arranged adjacent to each other; or in other words, the two parts 16, 17 are nested within each other and form together the central tubular cavity 12 in the form of a longitudinally sectioned half tube for receiving the medicament delivery device 3.

In this example, the first part 16 comprises the cut out 11, such that the second part 17 is accessible through the cut out 11, as shown in FIG. 8.

Further, the first part 16 comprises a circumferential rim 161, 162 on both terminal sections, providing a seating for a second cap 14 and a first cap 13, whereby the circumferential rims 161, 162 have attachment members 163 as shown in FIG. 9. The attachment members 163 are configured to securely fasten the second cap 14 onto the rim 162 and the first cap 13 onto the rim 161 as shown on FIG. 9. The attachment members 163 can be any suitable type, for example in form of threads, bayonet locking mechanisms, snap fit mechanisms, Velcro, glue, hooks, and/or magnets. The second cap closes the opening of the tubular body 101 such that the medicament delivery device cannot slide out of the central tubular cavity 12 through the opening. The first cap 13 comprises a circumferential ring 130 configured to be mounted on the upper rim 161 of the first part 16, wherein the first cap is fastened to the first part 16 with the members 163. The first cap further comprises an opening 132. From the circumferential ring 130 towards the central point of this opening 132, tapered arms 131 extend in the direction of the central point of the opening 132 as shown in FIG. 9.

Figure 10:
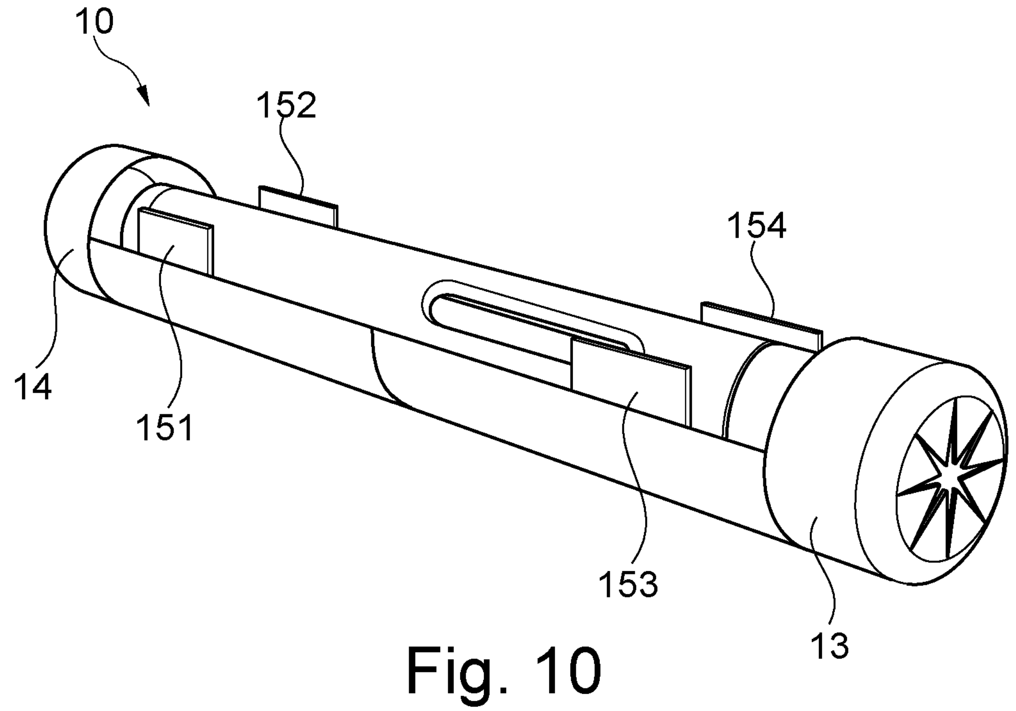
FIG. 10 is a perspective view of the storage container 10 of FIG. 7.
Figure 11:
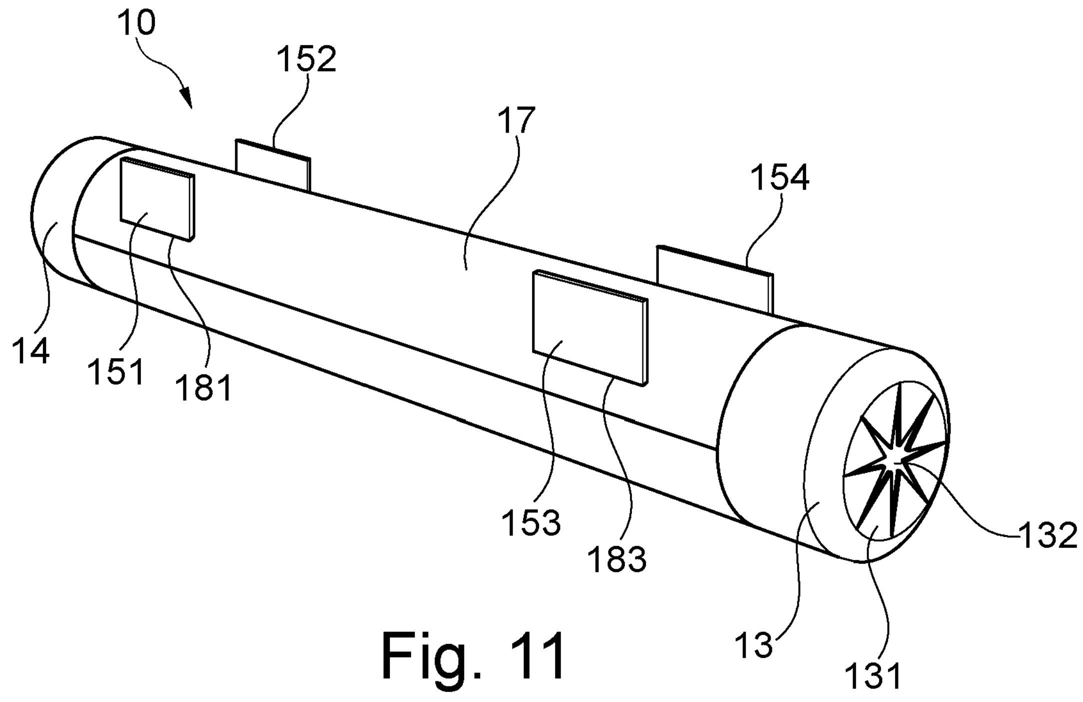
FIG. 11 is a perspective view of the storage container 10 transformed into a disposable medicament delivery device container.

The second part 17 comprises recesses in form of slits or holes 181, 182, 183, 184, 185 for example, which are configured to receive holding and fastening protrusions 151, 152, 153, 154 which protrude out of the first part 16 and are received by the respective recesses 181, 182, 183, 184, 185 as is illustrated in FIGS. 9 to 11 although the recesses 182 and 184 are not shown in FIGS. 9 to 11.

It is to be understood that the holding and fastening elements can be of any suitable type such as a folded section of the wall of the first part or a flexible hook, for example.

As shown in FIG. 10 the holding and fastening protrusions 151, 152, 153, 154 are configured to extend out of the tubular cavity 12 adjacent to the medicament delivery device 3 that is located in the cavity, such that the fastening elements 151, 152, 153, 154 provide additional lateral support for the medicament delivery device 3 during transport and storage. In general, provision of fastening elements 151, 152, 153, 154 is optional, but can be beneficial to help secure the medicament delivery device in the storage container.

After the medicament delivery device is unpacked, i.e. taken out of the central tubular cavity 12 and used, the medicament delivery device 3 is disposable if it is a single use device. Alternatively, the medicament delivery device may be a reusable device such as a multi dose device, in which case the medicament delivery device may be stored in the central tubular cavity 12 of the storage container 10 after use until the medicament delivery device becomes disposable. At this stage, the storage container 10 is transformable into a disposable medicament delivery device container configured to receive the medicament delivery device 3 as shown in FIG. 11.

Figure 12:
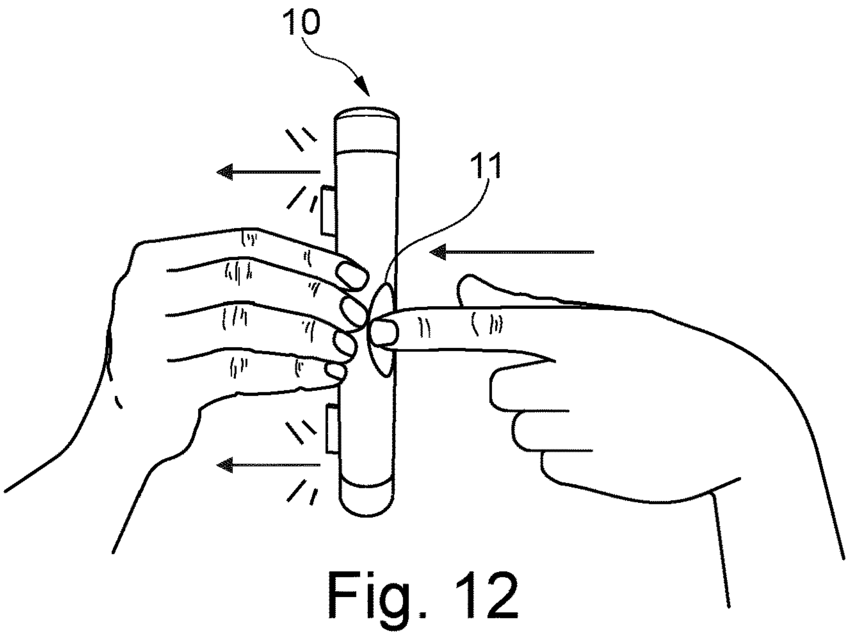
FIG. 12 shows the first handling step for transforming the storage container 10 into a disposable medicament delivery device container.
Figure 13:
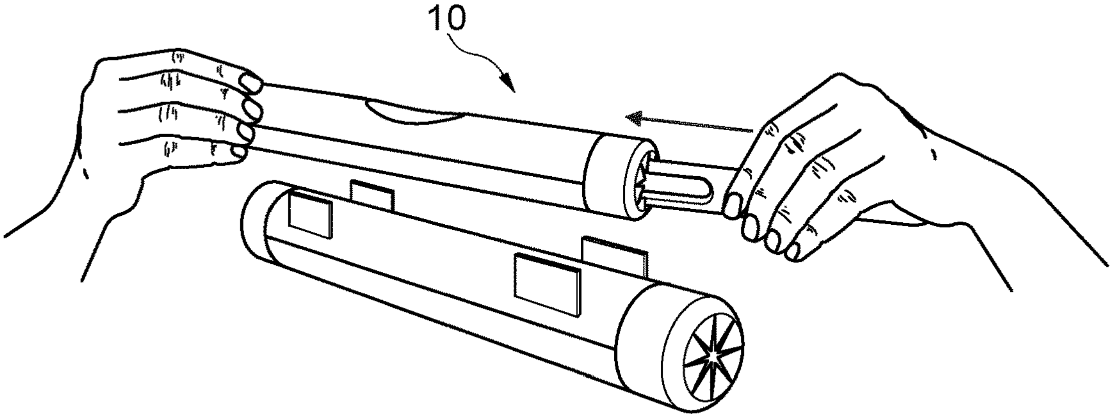
FIG. 13 shows the second handling step for transforming the storage container 10 into a disposable medicament delivery device container.
Figure 14:
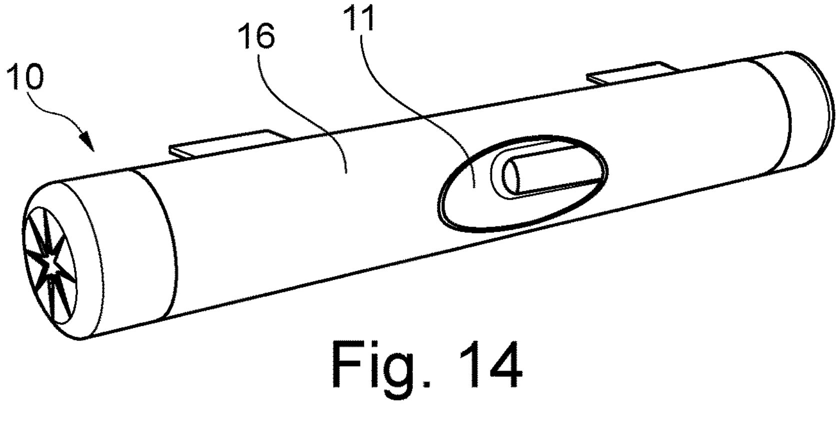
FIG. 14 shows the disposable medicament delivery device container 10 as a result of the transformation.

The transformational steps are illustrated in FIGS. 12 to 14, wherein in a first step the user holds the storage container 10 in one hand such that the cut out 11 on the rear side is accessible, then with a finger for example (or any suitable item for exerting pressure on the wall of the second part), the user pushes into the cut out 11 thereby exerting a force on the second part 17 such that the second part 17 deflects and inverses its curvature. Thereby the recesses 181, 182, 183, 184, 185 allow the fastening elements 151, 152, 153, 154 to slide through the recesses. As shown in FIGS. 11 and 13 the fastening elements 151, 152, 153, 154 extend and protrude out of the second part 17 thus providing a structural stability to the second part 17 in its deflected state. In this state the two parts 16 and 17 are not laying adjacent to each other, but form together a closed tubular body, i.e. the central tubular cavity 12 has been replaced by the first part 16 and the second part 17 forming together a third cavity, which is a closed central tubular cavity (this can also be seen as a combination of the first cavity and a third cavity). The container 10 is now a closed disposable medicament delivery device container. Next as shown on FIG. 13 the user can introduce the disposable medicament delivery device into the tubular body of the disposable medicament delivery device container 10 via the opening 132 such that the arms 131 bend under the applied force in the direction of movement and thus let the disposable medicament delivery device be introduced into the cavity of the disposable medicament delivery device container. After the passage of the medicament delivery device 3 through the opening 132, the arms 131 flex back to their initial position, thereby preventing the medicament delivery device 3 from slipping out. The arms 131 are configured to bend when a force is applied when introducing the disposable medicament delivery device into the cavity, but the weight of the medicament delivery device is not sufficient for bending the arms 131, accordingly the medicament delivery device cannot fall out of the cavity only by the weight of the medicament delivery device 3 applied on the arms 131.

The cross-sectional shape of the central tubular cavity 12 formed by the two parts can be of any suitable form, and would typically be chosen based on the shape of a medicament delivery device that is designed to fit in the cavity. The example of FIGS. 7 to 14 illustrate a circular cross-sectional shape of the central tubular cavity 12 in the plane perpendicular to the longitudinal axis. An elliptical, rectangular or triangular shape of the cross-section of the central tubular cavity 12 is also possible, for example.

Figure 15A:
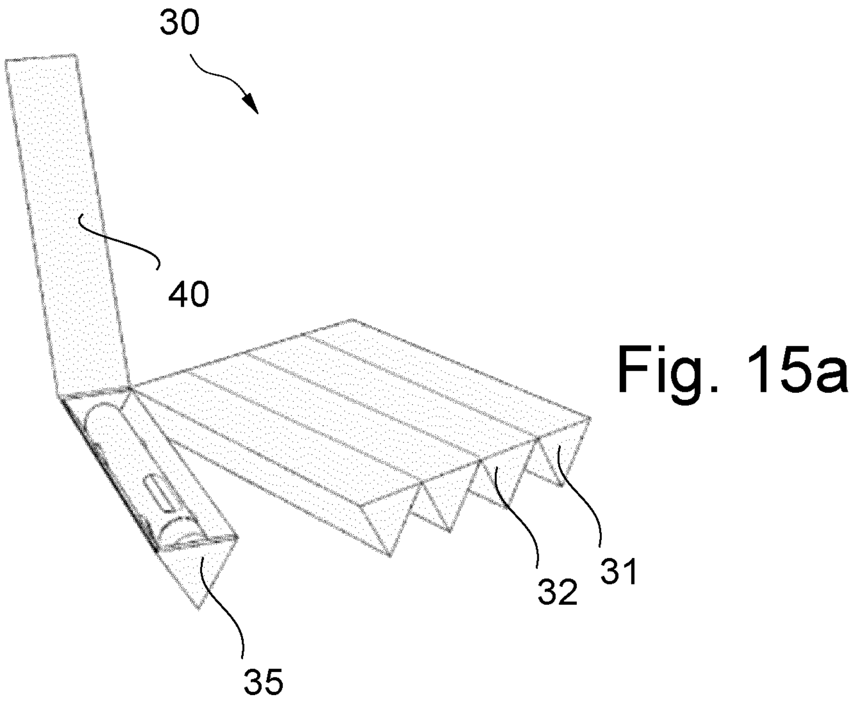
FIGS. 15A, 15B and 15C show perspective views of options for attaching multiple storage containers together, with FIG. 15A including a storage container open and detached for comparison.
Figure 15B:
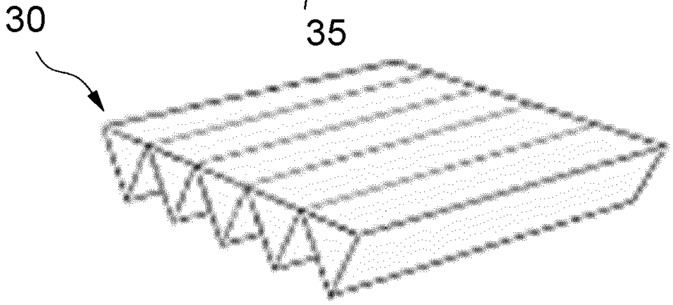
Figure 15C:
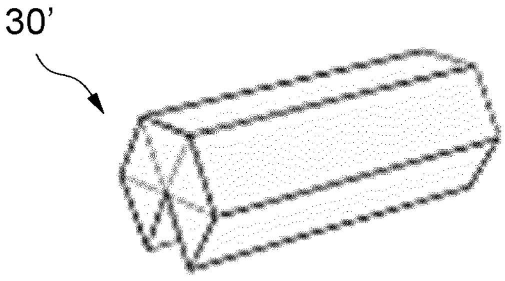

An example for the triangular shape is shown in FIGS. 15*a* to *c*. One advantage of a triangular shape is the possibility to build compact multipacks of medical delivery devices. FIGS. 15*a* and 15*b* show a row of storage containers 30 for medical delivery devices. One triangular storage container 31 is attached to an identical triangular storage container 32, which is also attached to an identical triangular storage container etc. thereby building a row of storage containers 30 for packaging and transport of the medical delivery devices, as shown in FIG. 15*a*, stored in the cavity of the storage containers.

FIG. 15*c* shows five triangular storage containers rolled up to a hexagonal compact storage unit 30' of five individual and joined triangular storage containers 31 to 36. Optionally in this example each storage container 31 to 35 may comprise a seal 40, which closes and seals the respective medicament delivery device in the cavity. This packaging unit is very compact and needs less space. As shown in the figure there is a space between the first and the fifth triangular storage container. A sixth triangular storage container can be added (not shown in the figures), filling the space between the first and the fifth triangular storage container.

Each individual triangular storage container is convertible into a disposable medicament delivery device container by deflection of a portion of one of the parts of the container as described in detail above.

The triangular storage container 30 has a longitudinal triangular tube shape extending along an axis L and comprises a body, the body having a front side and a rear side along the axis L. The body comprises on the front side a central cavity extending from one end to the other end of the body. The central cavity has a longitudinal opening; in other words, the central cavity defines a shape of a longitudinally sectioned triangular half tube whereby one end of the tubular body is closed, and the other comprises a triangular opening. From the edges of the triangular opening towards the central point of this opening, tapered arms (not visible in the figures) extend in the direction of the central point of the triangular opening. The central cavity is configured to receive the medicament delivery device 3. On the rear side of the body optionally there is a cut-out section. The body comprises two parts in the form of two half-shells arranged adjacent to each other; or in other words, the two parts are nested within each other and form together the central cavity in the form of a longitudinally sectioned triangular half tube for receiving the medicament delivery device 3.

In this example, the first part comprises the cut out (not visible in the figures), such that the second part is accessible through the cut out.

The second part comprises recesses in form of slits or holes for example (not visible in the figures), which are configured to receive holding and fastening protrusions which protrude out of the first part and are received by the respective recesses.

It is to be understood that the holding and fastening elements can be of any suitable type such as a folded section of the wall of the first part or a flexible hook, for example.

The holding and fastening protrusions are configured to extend out of the central cavity adjacent to the medicament delivery device 3 that is located in the cavity, such that the fastening elements provide additional lateral support for the medicament delivery device 3 during transport and storage. In general, provision of fastening elements is optional, but can be beneficial to help secure the medicament delivery device in the storage container.

After the medicament delivery device is unpacked, i.e. taken out of the central cavity and used, the medicament delivery device 3 is disposable if it is a single use device. Alternatively, the medicament delivery device may be a reusable device such as a multi dose device, in which case the medicament delivery device may be stored in the central cavity of the storage container 30 after use until the medicament delivery device becomes disposable. At this stage, the storage container 30 is transformable into a disposable medicament delivery device container configured to receive the medicament delivery device 3.

The transformational steps are illustrated for the storage container 10 in FIGS. 12 to 14 are not explicitly shown for the triangular storage container 30, as they are the same for the triangular storage container 30.

An alternative first cap not shown in the figures does not have a central opening but is a closed cap which can be pulled off the tubular body before the used medicament delivery device is introduced and then put back on the tubular body again. Optionally the first cap and the circumferential ring 130 have threaded, snap fit or magnetic means configured to engage with each other releasably and securely hold the first cap attached to the tubular body 101.

Figure 17:
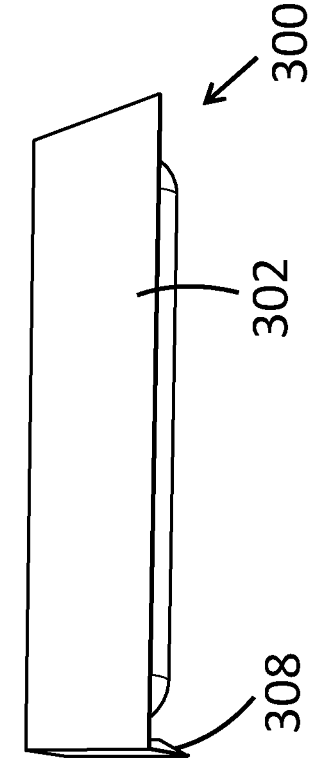
FIGS. 16 and 17 show perspective views of another example storage container when open and closed.
Figure 16:
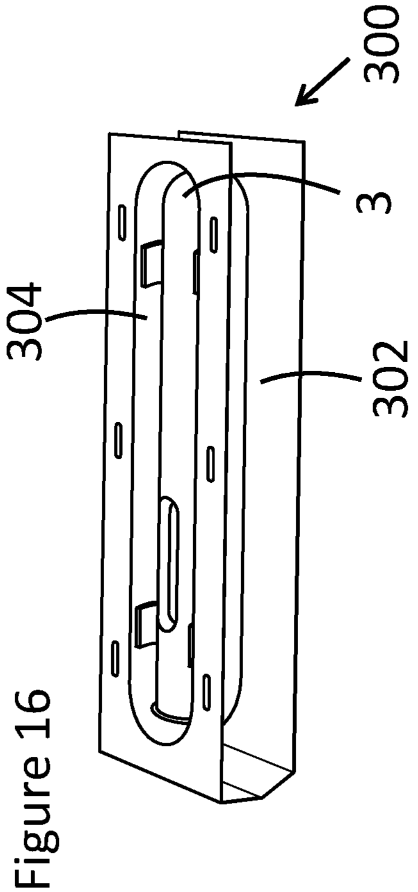

Another alternative storage container 300 is shown in FIGS. 16 to 17. The storage container comprises a first part comprising a cavity 304 configured to hold a medicament delivery device 3 (in this example an autoinjector). The storage container comprises a second part comprising a cover 302 configured to cover the cavity 304. The first part is attached to the second part by a hinge 308. Initially, the storage container is as shown in FIG. 17 (first or initial position), with the cover 302 closing the cavity 304 (for example with an airtight seal). The cover 302 can then be removed (to a second position) to access and use the medicament delivery device 3 (first step). Subsequently, the medicament delivery device can be placed back in the cavity 304 and the cover 302 can be moved back to its initial position (second step), closing the cavity. Unlike in various other designs described herein, the storage container is the same shape before and after medicament delivery device use.

Figure 19:
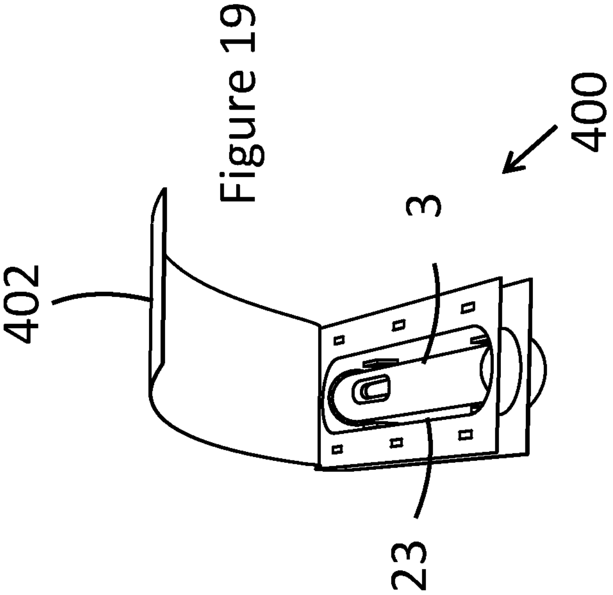
FIG. 19 shows a perspective view of a single storage container from the multiple storage containers of FIG. 18.
Figure 18:
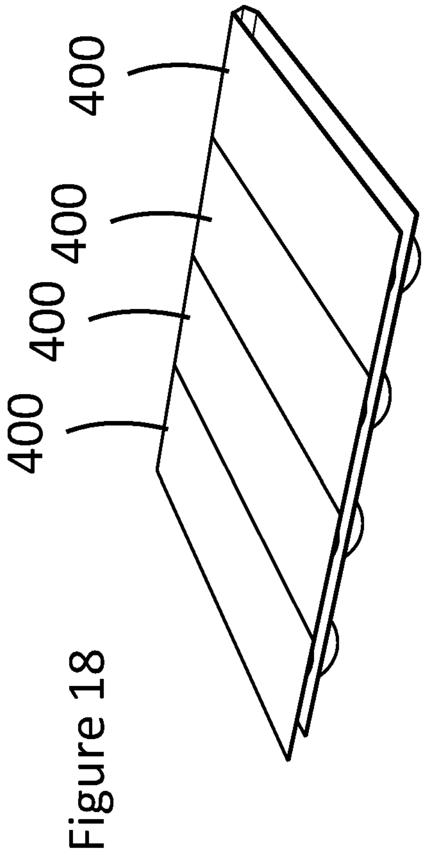
FIG. 18 shows a perspective view of another example of multiple storage containers attached together.
Figure 20:
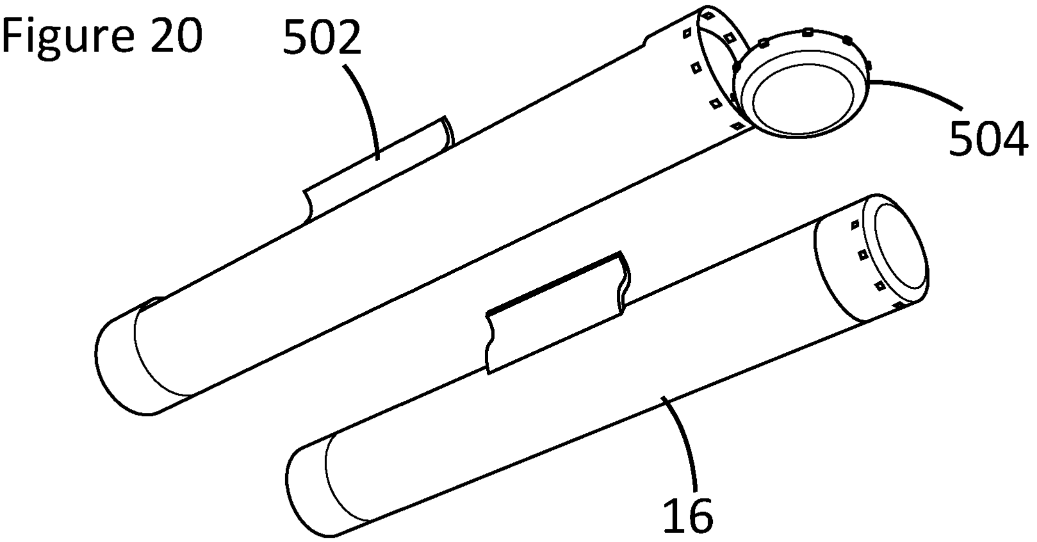
Figure 21:
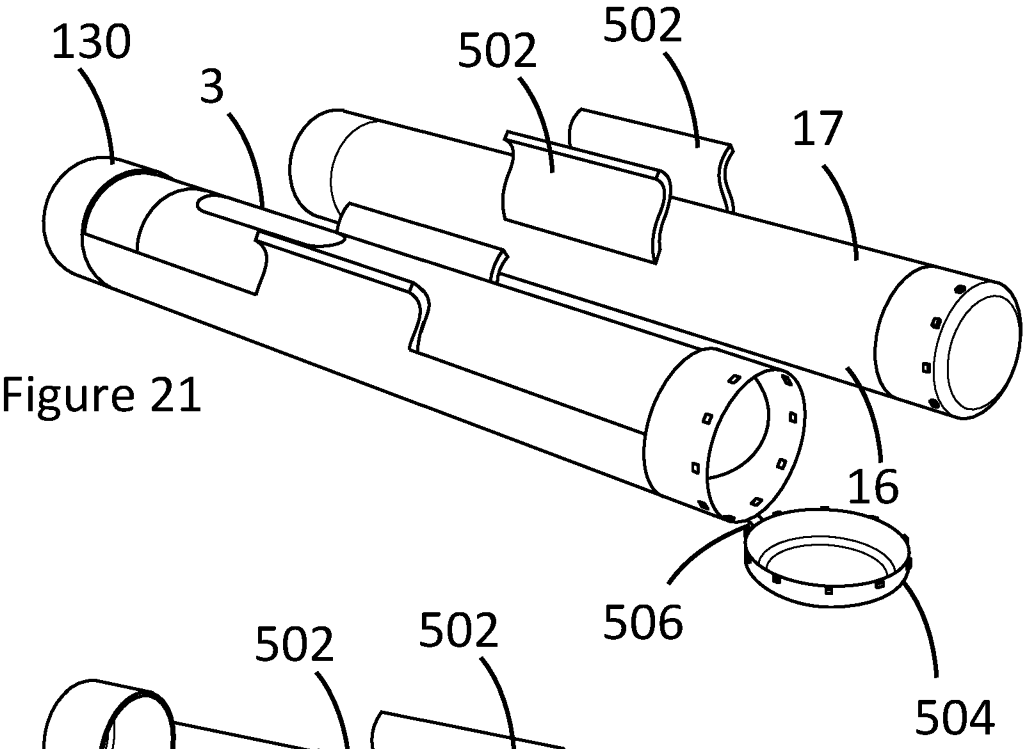
Figure 22:
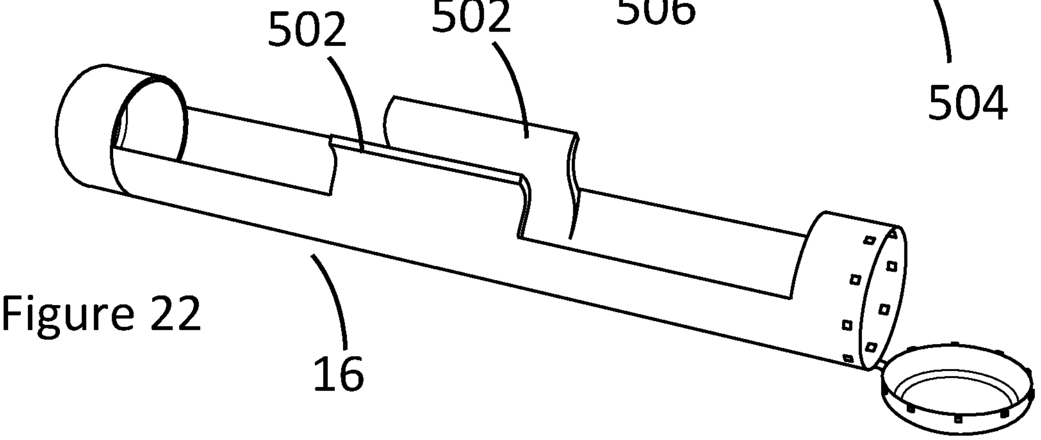

Another alternative storage container 400 is shown in FIGS. 18 to 19. Optionally, a plurality of storage containers 400 can be provided together as shown in FIG. 18. This can allow for a plurality of medicament delivery devices, such as the supply for a time period or for a course of treatment, to be provided together, or for simpler handling during bulk transport. The storage containers 400 can be detachably attached to one another, with a single storage container 400 shown in FIG. 19 and a set of four storage containers 400 attached together in FIG. 18, though more or fewer storage containers could alternatively be attached together. Each individual storage container 400 is basically equivalent to the design shown in FIGS. 1 to 3 and reference should be made to the description of FIGS. 1 to 3 for further details. In addition to the features shown in FIG. 1, a cover 402 is also visible in FIGS. 18 and 19; in particular, the cover can be seen partially removed in FIG. 19. The cover 402 is optional and can seal the cavity and/or protect the medicament delivery device during transport and/or prior to use, for example. A cover such as the cover 402 shown in FIGS. 18 and 19 could optionally be included on other examples shown herein, such as the example in FIGS. 1 to 3.

Another alternative storage container 500 is shown in FIGS. 20 to 24. This design is similar to the design in FIGS. 7 to 14 apart from the differences outlined below, and reference should be made to the description of FIGS. 7 to 14 for further details. In the example in FIGS. 20 to 26, a cut out 11 is not provided, which can provide a fully enclosed space for a medicament delivery device such as an autoinjector. In the example in FIGS. 20 to 26, a second cap 504 that is pivotable relative to the rest of the storage container due to a hinge 506 attaching the cap to the rest of the storage container is provided, so that the second cap remains attached to the storage container 500, rather than a second cap 14 that can be fully removed. Finally, the fastening elements 151, 152, 153, 154 of the design in FIGS. 7 to 14 are replaced by more ergonomically shaped pull tabs 502 in the design in FIGS. 20 to 26. Though this is not directly visible in the Figures, the pull tabs 502 would be attached in the manner shown in FIGS. 9 to 12, so that when the pull tabs are pulled, this exerts a force on the second part 17 such that the second part 17 deflects and inverses its curvature. The particular shape of the pull tabs 502 as shown in the Figures is optional, though, and could be changed, for example to the shape of the fastening elements 151, 152, 153, 154 of FIGS. 7 to 14. Another slightly different storage container 500 is shown in FIGS. 25 to 26; this design is similar to the design in FIGS. 20 to 24 apart from the differences outlined below, and reference should be made to the description of FIGS. 20 to 24 for further details. In the example in FIGS. 25 and 26, the circumferential ring 130 is an integral part of the storage container rather than being a removable part of the storage container, and the second cap 14 from FIGS. 7 to 14 is used rather than the second cap 504 from FIGS. 20 to 24.

Figure 27:
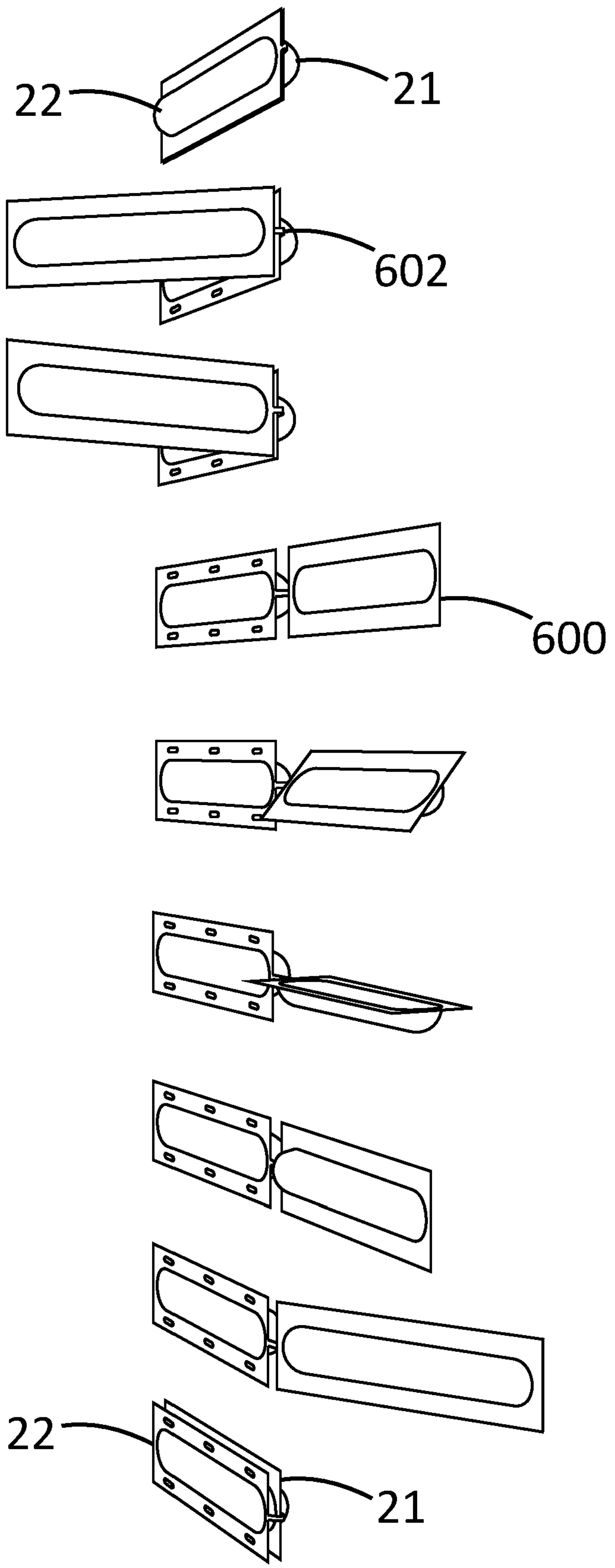
FIG. 27 shows perspective views of another storage container, shown in various stages of use.

FIG. 27 shows another storage container 600. The storage container is shown in nine stages, starting from an initial state as shown at the bottom of the page (i.e. configured to contain an unused medicament delivery device) to a final state as shown at the top of the page (i.e. configured to contain a used medicament delivery device). The basic structure of the first part 21 and the second part 22 are as described elsewhere herein and will not be repeated. Unlike in various other designs described herein, the two halves (namely the first part and the second part) of the storage container are the same shape before and after medicament delivery device use, although storage container is not the same shape as the positions of the two halves relative to one another are different. The two halves are attached to one another by a joint, which comprises a flexible strip that is an integral part of the storage container in this example (with the storage container preferably formed as a single integral piece), although the hinge could alternatively be a different type of twistable or rotatable joint. Because of the twistable or rotatable joint, the position of the second half 22 relative to the first half 21 can be rotated 180 degrees, thereby transitioning the storage container from the initial state (first configuration) to the final state (second configuration) without deformation of the second half 22.

Figure 28:
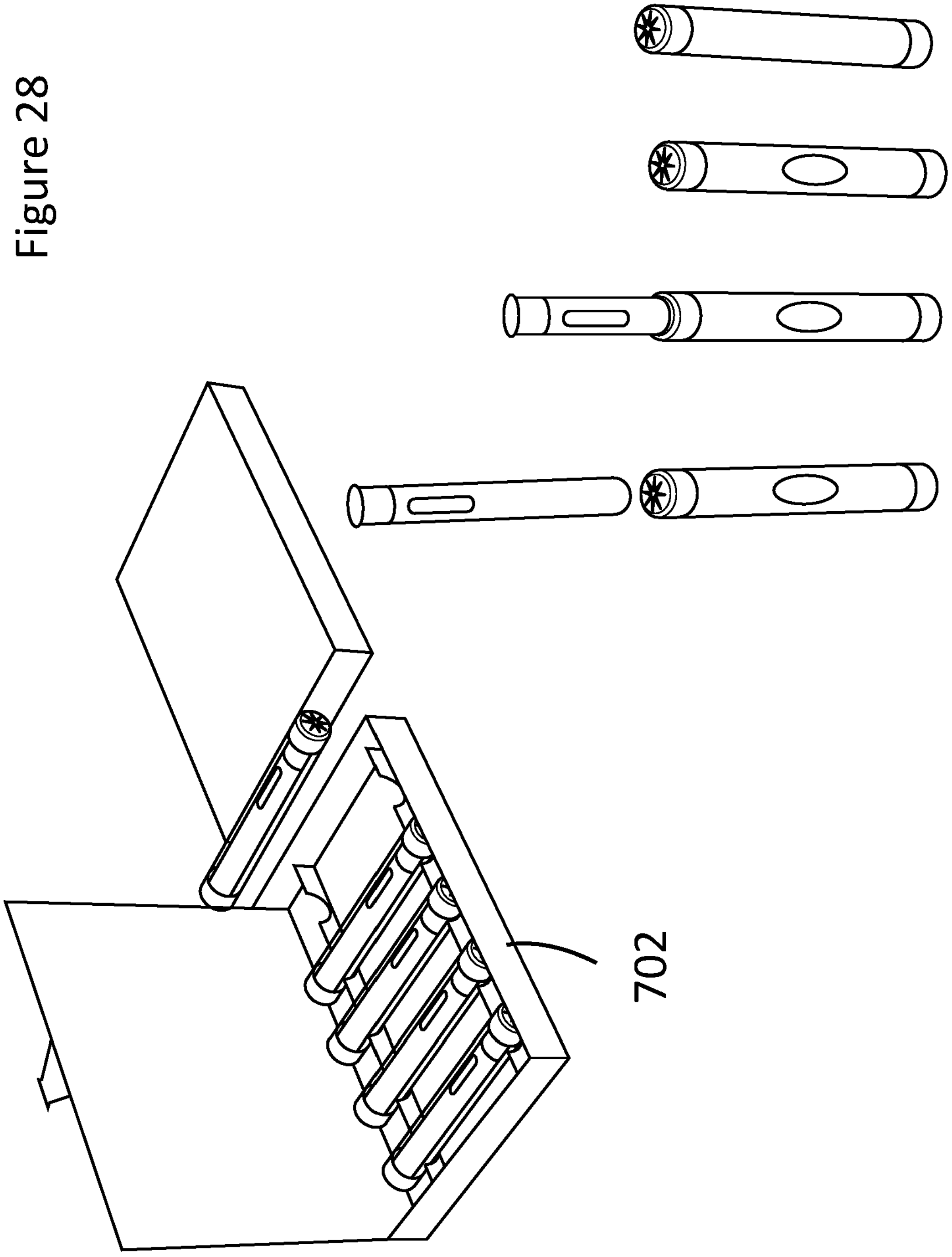
FIG. 28 shows views of a possible product comprising a storage container, shown in various stages of use.

FIG. 28 shows views of a possible product comprising a storage container such as the storage container in FIGS. 7 to 14 in various stages of use. A box 702 can comprise a plurality (2 or more, but 5 in this example) of storage containers, each containing a medicament delivery device (in this example an autoinjector).

Figure 29:
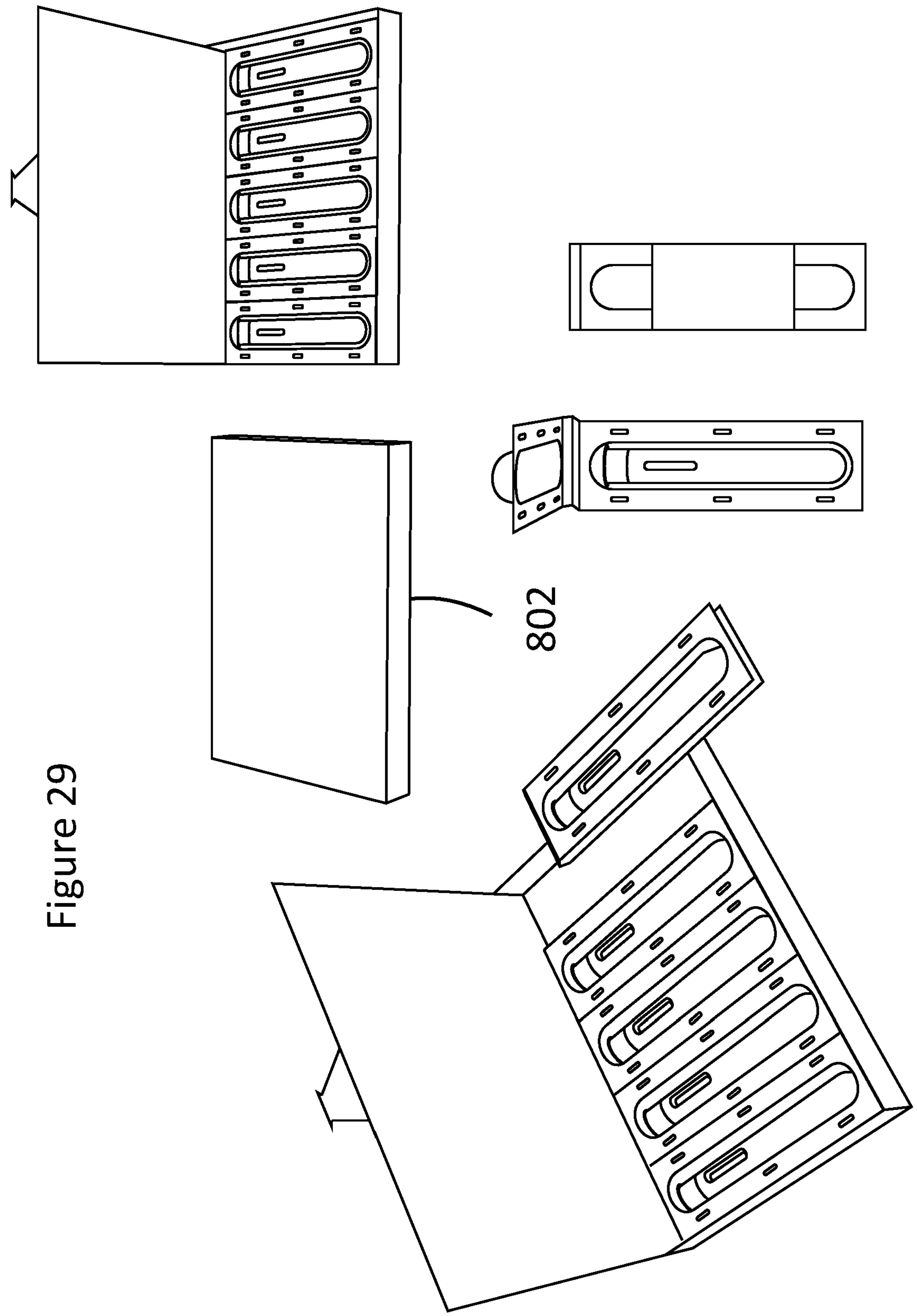
FIG. 29 shows views of another possible product comprising a storage container, shown in various stages of use.

FIG. 29 shows views of another possible product comprising a storage container such as the storage container in FIGS. 1 to 3 in various stages of use. A box 802 can comprise a plurality (2 or more, but 5 in this example) of storage containers, each containing a medicament delivery device (in this example an autoinjector).

Optionally, a label such as a shipping label could be added to the storage container after the medicament delivery device has been inserted into the storage container after medicament delivery device use; this would allow the user to dispose of the medicament delivery device by post. Returning the medicament delivery device in this way could help facilitate refurbishment, recycling or destruction of the medicament delivery device. This can help improve sustainability.

Optionally, the storage container comprises a connectivity unit, for example comprising an RFID tag. This could help with identifying the medicament delivery device at one or more points during the lifecycle of the device, including manufacture, packaging, use, disposal and/or recycling.

Various modifications to the embodiments described are possible and will occur to those skilled in the art without departing from the invention which is defined by the following claims.

Example methods and systems are described herein. It should be understood that the words "example," "exemplary," and "illustrative" are used herein to mean "serving as an example, instance, or illustration." Any embodiment or feature described herein as being an "example," being “exemplary,” or being “illustrative” is not necessarily to be construed as preferred or advantageous over other embodiments or features. The example embodiments described herein are not meant to be limiting. It will be readily understood that the aspects of the present disclosure, as generally described herein, and illustrated in the figures, can be arranged, substituted, combined, separated, and designed in a wide variety of different configurations, all of which are explicitly contemplated herein.

Furthermore, the particular arrangements shown in the Figures should not be viewed as limiting. It should be understood that other embodiments may include more or less of each element shown in a given Figure. Further, some of the illustrated elements may be combined or omitted. Yet further, an example embodiment may include elements that are not illustrated in the Figures.

Unless otherwise indicated, the terms “first,” “second,” etc. are used herein merely as labels, and are not intended to impose ordinal, positional, or hierarchical requirements on the items to which these terms refer. Moreover, reference to, e.g., a “second” item does not require or preclude the existence of, e.g., a “first” or lower-numbered item, and/or, e.g., a “third” or higher-numbered item.

As used herein, apparatus, element and method “configured to” perform a specified function is indeed capable of performing the specified function without any alteration, rather than merely having potential to perform the specified function after further modification. In other words, the apparatus, element, and method “configured to” perform a specified function is specifically selected, created, implemented, utilized, programmed, and/or designed for the purpose of performing the specified function. As used herein, “configured to” refers to existing characteristics of an apparatus, element, and method which enable the apparatus, element, and method to perform the specified function without further modification. For purposes of this disclosure, an apparatus, element, and method described as being “configured to” perform a particular function can additionally or alternatively be described as being “adapted to” and/or as being “operative to” perform that function.

Further, the wording medicament delivery device will be used herein. In this context, medicament delivery devices may include a number of devices capable of delivering certain doses of medicament to a user. The medicament delivery devices may be of either disposable or re-usable and may be provided with medicament containers suitably arranged for use of the medicament.

It will be appreciated that other arrangements are possible as well, including some arrangements that involve more or fewer steps than those described above, or steps in a different order than those described above.

Generally, all terms used in the claims are to be interpreted according to their ordinary meaning in the technical field, unless explicitly defined otherwise herein. All references to a/an/the element, apparatus, member, component, means, etc. are to be interpreted openly as referring to at least one instance of the element, apparatus, member component, means, etc., unless explicitly stated otherwise.

While various aspects and embodiments have been disclosed herein, other aspects and embodiments will be apparent to those skilled in the art. All embodiments within and between different aspects of the devices and methods can be combined unless the context clearly dictates otherwise. The various aspects and embodiments disclosed herein are for purposes of illustration and are not intended to be limiting, with the true scope and spirit being indicated by the claims.

The invention claimed is:

1. A storage container for a medicament delivery device, the storage container comprising a first part and a second part, wherein the first part is attached to the second part, wherein the first part comprises a first wall defining a first cavity, wherein the second part comprises a second wall defining a second cavity, and wherein the storage container is configured to change shape from a first configuration for storing the medicament delivery device prior to use to a second configuration for storing a used medicament delivery device, wherein the second wall is configured to invert from a first position in the first configuration to a second position in the second configuration, wherein the second wall defines a third cavity when in the second position, wherein the third cavity is the same shape as the second cavity.

2. The storage container of claim 1, wherein the second wall is in the first cavity in the first configuration.

3. The storage container of claim 1, wherein in the first configuration the second cavity is shaped to snugly receive said medicament delivery device prior to use.

4. The storage container of claim 1, wherein the second wall is flexible.

5. The storage container of claim 1, wherein a combination of the first cavity and the third cavity is shaped to snugly receive said used medicament delivery device.

6. The storage container of claim 1, wherein the first wall of the first part is configured to snugly receive the second wall of the second part.

7. The storage container of claim 1, wherein the storage container further comprises closing members for enclosing the used medicament delivery device in the storage container when in the second configuration.

8. The storage container of claim 1, wherein the first part is attached to the second part by a hinge.

9. The storage container of claim 1, wherein the first part comprises a first circumferential rim and the second part comprises a second circumferential rim, and the first circumferential rim is attached to the second circumferential rim.

10. A method for changing the shape of the storage container of claim 1 from the first configuration to the second configuration, comprising the steps of:

taking the medicament delivery device out of the storage container when in the first configuration; and moving the second wall out of the first cavity so that the storage container is ready to receive a used medicament delivery device.

11. The method of claim 10, wherein moving the second wall comprises the step of rotating the second part about a hinge.

12. The method of claim 10, wherein moving the second wall comprises applying a force on the second wall of the second part to invert the cavity of the second part.

* * * * *